United States Patent [19]

Stoub

[11] Patent Number: 4,583,187
[45] Date of Patent: Apr. 15, 1986

[54] METHOD AND CIRCUIT FOR STABILIZING CONVERSION GAIN OF RADIATION DETECTORS OF A RADIATION DETECTION SYSTEM

[75] Inventor: Everett W. Stoub, Villa Park, Ill.

[73] Assignee: Siemens Gammasonics, Inc., Des Plains, Ill.

[21] Appl. No.: 462,839

[22] Filed: Feb. 2, 1983

[51] Int. Cl.$^4$ .................. G01T 1/20; G01D 18/00
[52] U.S. Cl. .................. 364/571; 364/527; 250/363 R; 250/252.1
[58] Field of Search .................. 364/527, 571; 250/363 R, 363 S, 354.1, 252.1

[56] References Cited

U.S. PATENT DOCUMENTS

| | | | |
|---|---|---|---|
| 3,011,057 | 11/1961 | Anger | 250/71.5 |
| 3,903,417 | 9/1975 | Peter | 250/361 X |
| 4,047,034 | 9/1977 | Auphan | 250/354 |
| 4,296,320 | 10/1981 | Miller | 250/369 X |
| 4,298,944 | 11/1981 | Stoub et al. | 364/515 |
| 4,316,257 | 2/1982 | Del Medico et al. | 364/527 |
| 4,323,977 | 4/1982 | Arseneau | 364/571 |

FOREIGN PATENT DOCUMENTS 0023639  2/1981  European Pat. Off. .

OTHER PUBLICATIONS

"Stabilizing Scintillation Spectrometers with Counting-Rate-Difference Feedback", by H. de Waard, Nucleonics, vol. 13, No. 7, Jul. 1955, 36–41.
"Direct Current Stabilization of Scintillation Counters Used with Pulsed Accelerators", by F. P. G. Valckx, Nuclear Instruments and Methods, 10 (1961) 234–236, North-Holland Publishing Company.

Primary Examiner—Edward J. Wise
Attorney, Agent, or Firm—John Francis Moran

[57] ABSTRACT

A method and a circuit are provided for tuning or calibrating the gain of the radiation detectors of a radiation detection system. For each radiation detector tuning point the energy map status is measured in parallel. Thereby an energy response vector is obtained, which is multiplied with a predetermined deconvolution matrix. The deconvolution matrix is the inversion of a contribution matrix containing matrix elements $C_{ij}$, each such matrix element $C_{ij}$ of said contribution matrix representing the relative contribution level of a radiation detector j of said detection system for a point radiation source placed at a location i. Thus a calculated gain vector is obtained with respect to which the gains of the radiation detectors are adjusted such that an ideal gain vector is obtained.

12 Claims, 5 Drawing Figures

METHOD AND CIRCUIT FOR STABILIZING CONVERSION GAIN OF RADIATION DETECTORS OF A RADIATION DETECTION SYSTEM

BACKGROUND OF THE INVENTION

1. Field of the Invention

This invention relates to a method and a circuit for stabilizing the gain of raditaion detectors of a radiation detection system. In particular, this invention relates to the gain stabilization of photomultiplier tubes of a gamma scintillation camera.

2. Description of the Prior Art

Radiation detectors are widely used as diagnostic tools for analyzing the distribution of a radiation-emitting substance in an object under study, such as for the nuclear medical diagnosis of a human body organ. A typical radiation detector of a type which the present invention relates is a commercial version of the Anger-type scintillation camera, the basic prinicples of which are described in Anger U.S. Pat. No. 3,011,057.

Such a scintillation camera can take a "picture" of the distribution of radioactivity throughout an object under investigation, such as an organ of the human body which has taken up a diagnostic quantity of a radioactive isotope. As individual gamma rays are emitted from the distributed radioactivity in the object and pass through a collimator, they produce scintillation events in a thin planar scintillation crystal. The events are detected by photodetectors positioned behind the crystal. Electronic circuitry translates the outputs of the photodetectors into X and Y coordinate signals which indicate the position in the crystal of each event and a Z signal which indicates generally the energy of the event and is typically used to determine whether the event falls within a preselected energy range (window) for inclusion in the formation of the image. A picture of the radioactivity distribution in the object may be obtained by coupling the X and Y signals which fall within the preselected energy window to a display, such as a cathode ray oscilloscope which displays the individual scintillation events as spots positioned in accordance with the coordinate signals. The detection circuitry typically provides for integrating a large number of spots onto photographic film.

Modern types of scintillation cameras which comprise circuitry for energy and linear spatial distortion correction are described for example in Stoub et al. U.S. Pat. No. 4,298,944, Arseneau U.S. Pat. No. 4,323,977 and Del Medico et al. U.S. Pat. No. 4,316,257. These modern cameras can provide virtually perfect precision of spatial response and uniformity of energy signal response, i.e. spatial linearity and a flat (constant) Z-map.

However, it is well known that in radiation detection systems, the gains of radiation detectors such as photomultiplier tubes in gamma scintillation cameras, change with age, with temperature, with instantaneous current, high voltage conditions, external fields, as well as other less obvious influences, such as voltage and current history. Due to these gain changes, there occurs subsequent tuning errors. If all the photomultiplier tubes in a camera should change in concert, the only effect would be a shift in the net signal amplitudes.

Such an effect could easily be accommodated by a circuitry as described in Miller U.S. Pat. No. 4,296,320 or in the study "Stabilizing Scintillation Spectrometers With Counting-Rate-Difference Feedback" by H. de Waard, Nucleonics Vol. 13, No. 7, July 1955, 36–41. In these cases the analyzer responds to a source of radiation embedded into the scintillation crystal and having a known peak in its energy spectrum. A high voltage regulator is provided, which adjusts the high voltage source of the photomultiplier tube so that the known peak in the energy spectrum corresponds to a desired pulse height.

Similar calibration methods and circuitry are described in the study "Direct Current Stabilization of Scintillation Counters Used With Pulsed Accelerators" by F. P. G. Valckx, Nuclear Instruments and Methods 10 (1961) 234–236, North-Holland Publishing Company; and Peter U.S. Pat. No. 3,903,417. While F. P. G. Valckx makes use of a constant light source, Peter applies to a so-called beta light for calibration.

However, it is never the case that all photomultiplier tubes exhibit gain changes of a uniform nature. Individual photomultiplier tube gain drifts differentially with respect to the average gain drift of the set and can, in short times for some photomultiplier tube types, yield substantial local z-map errors. Such local z-map errors, in turn, result in local sensitivity variations. These variations are mild for on-peak imaging circumstances (photopeak centered in the analyzer window) and measure to be about 1% sensitivity loss per KeV (shift) for the 140 KeV photopeak of 99mTc. Substantially greater sensitivity variations are present for off-peak imaging. These effects can easily be greater than 8% per KeV for a 7 KeV shift of the window to the high side of the 140 KeV photopeak.

Periodic gain calibration, i.e., tuning, service by camera technicians, utilizes a serial tuning algorithm, an example of which is, for instance, described in the European patent application No. 0,023,639. Such an algorithm is iterative. Most factory and field technicians use this approach today in tuning cameras.

However, the major difficulty in the serial tuning algorithm is related to the convolution effects of the photomultiplier tubes within the set. These convolution effects preclude a simple, direct photomultiplier tube gain adjustment in a camera system. Other difficulties are related to the perturbations to overall response due to phototube current changes and scintillator after glow characteristics when compact sources are used to selectively illuminate photomultiplier tubes in the detector head.

SUMMARY OF THE INVENTION

It is an object of the present invention to provide an improved method and circuit for tuning the radiation detectors of a radiation detection system, which allows a quick direct gain adjustment.

Another object of the present invention is to provide such an improved tuning method and circuit, particularly for the photomultiplier tubes of a gamma scintillation camera.

According to the present invention, a method for tuning the radiation detectors of a radiation detection system, in particular the photomultiplier tubes of gamma scintillation camera, is provided, which comprises the steps of:

(a) measuring in parallel for each radiation detector tuning point the energy map status, thereby obtaining an energy response vector, said tuning points being compact regions of the detector each being in proximity and corresponding in location to one of the radiation detectors;

(b) multiplying that energy response vector with a predetermined deconvolution matrix, said deconvolution matrix being the inversion of a contribution matrix containing matrix elements $C_{ij}$, each such matrix elements $C_{ij}$ of said contribution matrix representing the relative contribution level of radiation detector j of said detection system for a point radiation source placed at a location i, thereby obtaining a calculated gain vector for said radiation detectors;

(c) adjusting the gains of the radiation detectors with respect to the calculated gain vector, so as to correct for gain errors;

(d) measuring again the energy map status according to step (a); and (e) if the energy map status is not yet substantially ideal, repeat steps (b) to (d) until the energy map status is substantially ideal.

Further in connection with the present invention, a circuit for tuning the radiation detectors of a radiation detection system, in particular the photomultiplier tubes of a gamma scintillation camera is provided, which circuit comprises:

(a) means for measuring in parallel for each radiation detector tuning point the energy map status, thereby obtaining an energy response vector;

(b) means for multiplying said energy response vector with a predetermined deconvolution matrix, said matrix is the inversion of a contribution matrix containing matrix elements $C_{ij}$, each such matrix element $C_{ij}$ of said contribution matrix representing the relative contribution level of a radiation detector j of said detection system for a point radiation source placed at a location i, thereby obtaining a calculated gain vector for said radiation detectors;

(c) means for adjusting the gains of the radiation detectors with respect to said calculated gain vector, so as to correct for gain errors.

Thus a method and a circuit is provided which allow parallel tuning on the basis of matrix practice. Parallel tuning advantageously allows quick direct gain adjustment. In contrast to serial tuning, where the number of necessary correction steps corresponding to the total number of radiation detectors is relatively high, one-step corrections are possible with parallel tuning according to the present invention.

The foregoing and other objects, features and advantages of the invention will be apparent from the following more detailed description of preferred embodiments of the invention, as illustrated in the accompanying drawings.

Figure 1:
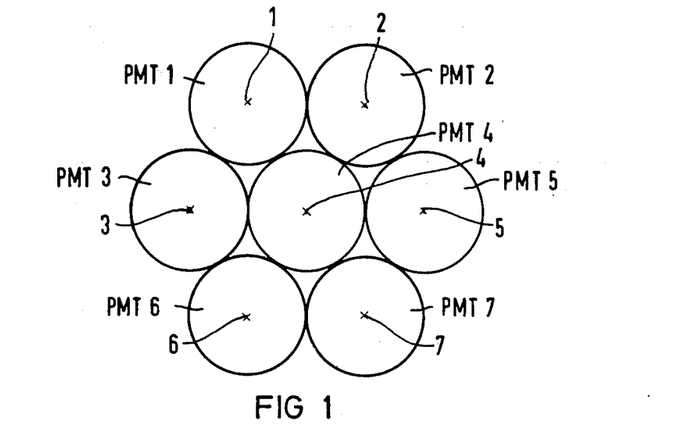
FIG. 1 shows a top view of an arrangement of for example seven photomultiplier tubes at the head of a gamma scintillation camera.

Common gamma scintillation cameras normally have between 37 and 75 photomultiplier tubes (PMT). However, in order to simplify the description, the distinction between prior art serial tuning and parallel tuning according to the present invention is described with respect to a simplified model 7 PMT camera, as shown in FIG. 1 of the drawings. In this camera, each of the seven photomultiplier tubes PMT #1 to PMT #7 has one source location point 1 to 7, all of these points together correspond to the tuning points of the 7 PMT camera.

A source of radiation placed, as an example, at position #1 (the tuning or calibration point for tube PMT #1) will result in 22% of the total signal being collected by the tube PMT #1, 14% each in tubes PMT #2 and PMT #3, 38% in tube PMT #4, 5% each in tubes PMT #5 and PMT #6, and only 2% in tube PMT #7. The reason that tube PMT #4 has a larger share of the signal than tube PMT #1 is due to two important influences:

First of all, the tuning point for tube PMT #1 is not dead center over tube PMT #1, but shifted radially inward towards the center of tube PMT #4. This reduces the relative signal of the PMT #1 immediately. The second important effect is the circular shape of the crystal which reflects light inward, thereby boosting tube PMT #4's signal. These two effects combine to yield the surprisingly high signal in tube PMT #4.

However, there is a great deal of symmetry in the camera of FIG. 1, as shown by the following table presenting in a matrix the relationship between "unit source location" and "relative PMT signal contribution":

| UNIT SOURCE LOCATION | RELATIVE PMT SIGNAL CONTRIBUTION | | | | | | |
|---|---|---|---|---|---|---|---|
| | 1 | 2 | 3 | 4 | 5 | 6 | 7 |
| 1: | .22 | .14 | .14 | .38 | .05 | .05 | .02 |
| 2: | .14 | .22 | .05 | .38 | .14 | .02 | .05 |
| 3: | .14 | .05 | .22 | .38 | .02 | .14 | .05 |
| 4: | .09 | .09 | .09 | .46 | .09 | .09 | .09 |
| 5: | .05 | .14 | .02 | .38 | .22 | .05 | .14 |
| 6: | .05 | .02 | .14 | .38 | .05 | .22 | .14 |
| 7: | .02 | .05 | .05 | .38 | .14 | .14 | .22 |

As can be seen from this matrix, six of the seven tubes PMT #1 to PMT #7 have the same symmetrical relationship to each other as tube PMT #1, so that the entries in all but row four of this matrix are merely scrambled values of the entries in row one. Row four reflects the central position of tube PMT #4, wherein it receives 46% of the signal for a source placed over tube PMT #4, while only 9% of the signal is collected by each of the remaining six tubes of the camera.

The matrix described above can be used to predict the energy response of the camera for any variety of combination of individual PMT gain levels. As an example, consider the case where all 7 PMT's have precisely the same gain, namely $G1 = G2 \ldots = G7 - 1$. Then $Z_1$, the z map level at the tuning point #1, can be calculated as the sum of seven products: the first product is the first entry of the matrix, 0.22, times the gain G1 of the first tube PMT #1, plus the product of 0.14, the second entry in the first row of the matrix, times the gain G2 of tube PMT #2, and so forth down to the last entry in row one, 0.02, times the gain G7 of tube PMT #7.

That running sum of products, $Z_1$, has a value 1.0000. This calculation can be repeated for every tube and, in this case, every tuning point will have exactly the same z-map value, namely 1.0000, as more precisely shown by the following table:

Let: $G_1 = 1.$
$G_2 = 1.$
.
.
.
$G_7 = 1.$
then, $Z_1 = .22 \times 1. + .14 \times 1. + \ldots + .02 \times 1. = 1.0000$
.
.
.
$Z_7 = .02 \times 1. + .05 \times 1. + \ldots + .22 \times 1. = 1.0000$ As a second example, consider the case where every tube has a tuning error or 5, 10, or 15% as indicated in the following table:

Let: $G_1 = 1.05$
$G_2 = 1.10$
$G_3 = 0.85$
$G_4 = 0.90$
$G_5 = 0.90$
$G_6 = 1.15$
$G_7 = 1.05$
then, $Z_1 = .22 \times 1.05 + .14 \times 1.10 + \ldots + .02 \times 1.05 = 0.9695$
.
.
.
$Z_7 = .02 \times 1.05 + .05 \times 1.10 + \ldots + .22 \times 1.05 = 0.9785$ Now to calculate $Z_1$, one takes that first entry of 0.22 times the gain of tube PMT #1, which is 1.05, plus the second entry in row one of the matrix, 0.14, times the gain of the second tube PMT #2, 1.1, plus the third entry times the gain of the third tube PMT #3, and so forth down to the last entry in row one of the matrix, 0.02, times 1.05, the gain of the last tube. That running sum, $Z_1$, is 0.9695, substantially different than the unit value obtained in the first example. This calculation can be repeated by using the appropriate rows of data and the appropriate gain levels to obtain the z-map estimates at every one of the seven tuning or calibration points. Every one of the seven tuning points now has a substantial z-map error.

In the prior art serial tuning, a serviceman arbitrarily places the point source over the tuning point of the central tube, in this case tube PMT #4, proceeding then to adjust the gain of tube PMT #4 in order to clear, or null, the z-map error present at that point. The process is mechanically simple: one identifies the tuning potentiometer and twists it one way or the other in order to null the z-map error as reported on the tuning meter. Next the service technician places the source over one of the tuning points in the next inner ring of tubes and adjusts the gain of the corresponding PMT in order to null the z-map error being reported at that point. Moving from point to point around the first ring, this technician will finally arrive at tube PMT #7, adjusting its gain in order to null the z-map error for the source at the tuning point of PMT #7. Now the algorithm proceeds by checking the z-map and repeating the individual tube adjustment steps until all z-map errors are small. Typically, a z-map error less than 0.3% is considered small.

The prior art serial tune algorithm as described above is again more precisely shown in the following table:

SERIAL TUNE ALGORITHM (1) Place source over PMT #4 and null z-map error
(2) Place source over PMT #1 and null z-map error
.
.
.
(7) Place source over PMT #7 and null z-map error
(8) Check z-map and repeat (1)–(7) until the z-errors are small ($<0.003$)

In order to test this algorithm on the 7 PMT camera, consider the following set of tube gains: gain G1, with a 10% error, at 1.1, gain G1 through gain G7 at unit gain, no error. Proceeding to step one of the tune algorithm, $Z_4$ reads 0.9% high before adjustment; after nulling, the gain of PMT #4, $G_4$, now reads 2% low. Proceeding with step two, adjusting $Z_1$, which reads 1.5% high before adjustment, yields a $G_1$ 3.4% high, a substantial reduction from the 10% high given as the initial condition. Following through this serial tune algorithm, the step for checking the z-map would reveal a Z error range of up to 0.5%. Therefore, the entire sequence of gain adjustments 1 through 7 would need to be repeated.

The test example is again more precisely shown by the following table:

| | Test |
|---|---|
| | Set $G_1 = 1.10$; $G_i = 1.00$, $i = 2$ to $7$ |
| (1) | $Z_4$ reads 1.0090 before adjustment; $G_4$ reads 0.9804 after adjustment; |
| (2) | $Z_1$ reads 1.0146 before adjustment; $G_1$ reads 1.0338 after adjustment; |
| (3) | $Z_2$ reads 0.9983 before adjustment; $G_2$ reads 1.0123 after adjustment; |
| . | |
| . | |
| (7) | $Z_7$ reads 0.9989 before adjustment; $G_7$ reads 1.0051 after adjustment; |
| (8) | $\vec{Z} = \begin{Bmatrix} 1.0048 \\ 1.0035 \\ 1.0027 \\ 0.9994 \\ 1.0015 \\ 1.0021 \\ 1.0000 \end{Bmatrix}$ i.e. more tuning needed |

As can be seen from this, the convolution effects of each PMT on other PMT's is a distinctive handicap in the serial tune algorithm. It yields a rather slow convergence on a well tuned state due to the convolution effects in the serial tune algorithm.

In contrast thereto a parallel tuning method according to the present invention allows faster direct gain adjustment.

This parallel tuning method requires the use of matrix methods. In order to simplify the description a summary of some general matrix notation techniques as applied to the present invention is made in the following table:

MATRIX NOTATION $\vec{C}$ contribution matrix
   elements: $C_{ij}$ = relative contribution level
   whereby
      i = tuning point source location; and
      j = PMT location
$\vec{G}$ gain vector
   components: $G_i$ = relative PMT gain level
   whereby i = PMT location
$\vec{Z}$ signal vector or Z-map
   components: $Z_i$ = Z-map value
   whereby i = tuning point source location

MATRIX ARITHMETIC $\vec{Z} = \vec{C} \cdot \vec{G}$ multiplication (convolution)

If $\vec{G} = \vec{1} + \vec{\Delta G}$ then $\vec{\Delta Z} = \vec{C} \cdot \vec{\Delta G}$ where $\vec{Z} = \vec{1} + \vec{\Delta Z}$ Consider the contribution matrix $\vec{C}$ containing elements $C_{ij}$. Each such element represents the relative contribution level of the photomultiplier tube j for a point source placed at tuning point location i. Consider also the gain vector $\vec{G}$ which has N components where N refers to the total number of photomultiplier tubes in the camera. Each component $G_i$ is the relative photomultiplier tube gain level for tube i. The Z signal vector, or z-map, has components $Z_j$, where j refers to the source location representing the relative z-map value of the camera response at that point. Matrix arithmetic may be defined for matrices. In particular, the matrix operation of multiplication, a convolution, can be defined in terms of individual component multiplications and running sums, identical to the operations performed in the serial tuning example.

Further simplifications in notation can be obtained using a unit vector $\vec{1}$ or unit matrix $\vec{1}$. In matrix form a unit matrix has all zero value components or matrix elements, except along the diagonal, where it has unit values. A unit vector has unit values for every component. In this form, the gain vector $\vec{G}$ can be defined as the sum of a unit vector and a gain error vector. Likewise, the z-map vector, $\vec{Z}$, can be defined as a unit vector plus a z-map error vector. The z-map error vector can be predicted by the multiplication of the contribution matrix against the gain error vector.

Matrix inversion can be performed for the matrix $\vec{C}$, if the matrix $\vec{C}$ is well behaved. This matrix inverse of $\vec{C}$ can deconvolve the z-map components to yield photomultiplier tube gain level directly.

The contribution matrix is measured once in off-line measurement.

This is performed by the following steps:
(1) place a radiation source at a tuning point #i;
(2) measure all radiation detector signals $Z_{ij}$, j being the detector number, individually with a signal amplitude measuring device, e.g. voltmeter;
(3) add individual $Z_{ij}$'s together to the total $Z_i$ signal for tuning point i according to the equation $$Z_i = \sum_{j=1}^{N} Z_{ij}$$

(4) repeat (1) through (3) for each of the N tuning points
(5) calculate $C_{ij}$ according to the equation $$C_{ij} = \frac{Z_{ij}}{Z_i}$$

(6) form the matrix $$\vec{C} = \begin{pmatrix} C_{11} & C_{12} & \ldots & C_{1N} \\ C_{21} & & & \cdot \\ \cdot & & & \cdot \\ \cdot & & & \cdot \\ \cdot & & & \cdot \\ C_{N1} & \ldots & \ldots & C_{NN} \end{pmatrix}$$

(7) calculate the deconvolution matrix $\vec{D} = \vec{C}^{-1}$.

An example of a deconvolution matrix $\vec{D}$ is shown by the following table, which represents the inverse matrix of the 7 PMT camera contribution matrix in a previous table:

| | DECONVOLUTION MATRIX ELEMENTS | | | | | | |
|---|---|---|---|---|---|---|---|
| | 1 | 2 | 3 | 4 | 5 | 6 | 7 |
| 1: | 17.11 | −10.13 | −10.13 | −4.75 | 5.38 | 5.38 | −1.86 |
| 2: | −10.13 | 17.11 | 5.38 | −4.75 | −10.13 | −1.86 | 5.38 |
| 3: | −10.13 | 5.38 | 17.11 | −4.75 | −1.86 | −10.13 | 5.38 |
| 4: | −1.12 | −1.13 | −1.13 | 7.75 | −1.12 | −1.12 | −1.13 |
| 5: | 5.38 | −10.13 | −1.86 | −4.75 | 17.11 | 5.38 | −10.13 |
| 6: | 5.38 | −1.86 | −10.13 | −4.75 | 5.38 | 17.11 | −10.13 |
| 7: | −1.86 | 5.38 | 5.38 | −4.75 | −10.13 | −10.13 | 17.11 |

Defining the deconvolution matrix as the matrix $\vec{D}$ equal to the inverse of $\vec{C}$, then the product of $\vec{D}$ with $\vec{C}$ will yield the unit matrix $\vec{1}$. The gain vector $\vec{G}$ can be obtained simply by multiplying the deconvolution matrix $\vec{D}$ against the z-map vector $\vec{Z}$.

A parallel tune algorithm can now be defined which uses these matrix methods. In contrast to the serial tune algorithm, every value of the z-map vector $\vec{Z}$ is measured in one measurement phase. Then, in order to make optimum use of the z-map vector, the deconvolution matrix $\vec{D}$ is applied to $\vec{Z}$ to estimate the gain vector $\vec{G}$ directly. This estimate is then used to adjust the individual photomultiplier tubes #1 to #7 accordingly. Finally, in a remeasurement phase, every component of $\vec{Z}$ is measured again and, if necessary, an application of $\vec{D}$ to $\vec{Z}$ and subsequently the PMT gain adjustment is repeated, until the Z errors are small.

The method of parallel tuning or gain calibration is again more precisely described in the following table:

PARALLEL TUNE ALGORITHM (1) Measure the Z-map $\vec{Z}$
(2) Apply the deconvolution matrix $\vec{D}$ to $\vec{Z}$ to obtain the gain vector $G_{est}$ estimate.
(3) Adjust the PMT gains accordingly.

(4) Measure the $\vec{Z}$-map Z and repeat (2) to (3) until the Z-errors are small (<0.003)

As a test case, consider the same example as before. First let gain $G_1$ be 1.10, all other gains equal to 1. The z-map has measured component errors ranging from 0.2% to 2.2%. This $\vec{Z}$ vector is multiplied by the deconvolution matrix $\overline{D}$ to get the gain estimate vector $\vec{G}_{est}$. Note that there may be round-off errors, the gain estimate faithfully reflects the test conditions. The resulting gain adjustment yield a new gain vector $\vec{G}'$ complete with round-off errors. Finally, the z-map components are again checked and now found to be equal to 1, within the accuracy of the listing.

The test conditions described above are again more precisely described in the following table:

Set $G_1 = 1.10; G_i = 1.00; i = 2$ to 7

(1)
$$\vec{Z} = \begin{Bmatrix} 1.022 \\ 1.014 \\ 1.014 \\ 1.009 \\ 1.005 \\ 1.005 \\ 1.002 \end{Bmatrix}$$

(2)
$$\vec{G}_{est} = \begin{Bmatrix} 1.1001 \\ 1.0001 \\ 1.0001 \\ 1.0000 \\ 1.9999 \\ 1.9999 \\ 1.9999 \end{Bmatrix}$$

(3)
$$\vec{G}' = \begin{Bmatrix} .9999 \\ .9999 \\ .9999 \\ 1.0000 \\ 1.0001 \\ 1.0001 \\ 1.0001 \end{Bmatrix}$$

(4)
$$\vec{Z}' = \begin{Bmatrix} 1.0000 \\ 1.0000 \\ 1.0000 \\ 1.0000 \\ 1.0000 \\ 1.0000 \\ 1.0000 \end{Bmatrix}$$

Figure 2:
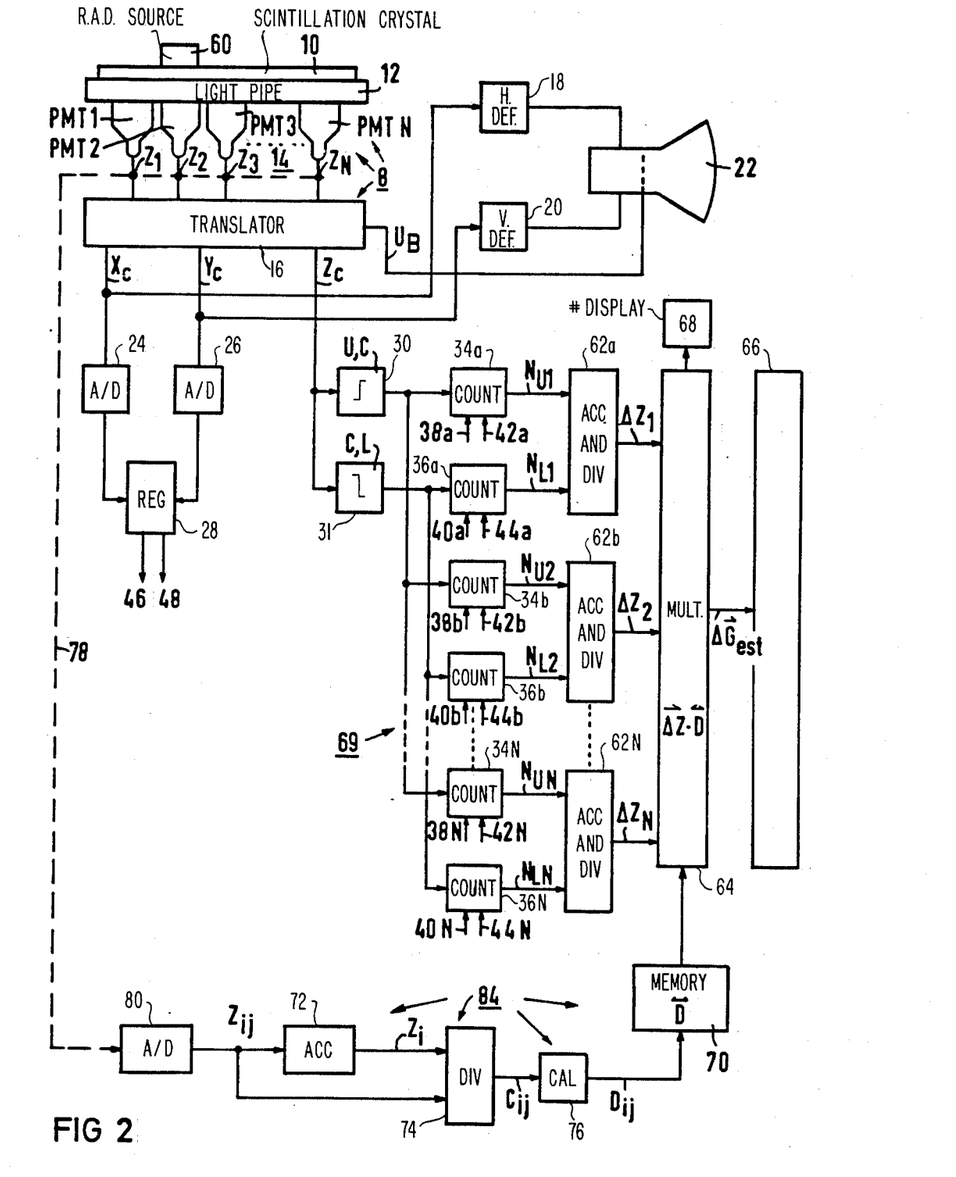
FIG. 2 shows a block circuit diagram for tuning the radiation detectors of a radiation detection system, such as the photomultiplier tubes of a gamma scintillation camera according to the invention.

A circuit for tuning the radiation detectors, such as photomultiplier tubes, of a scintillation camera according to the present invention is shown in FIG. 2.

An Anger-type scintillation camera is indicated with the numeral 8. The camera 8 comprises a scintillation crystal 10, a light pipe 12 and a set 14 of N photomultiplier tubes PMT1 to PMTN (e.g. N=37 or 75). The outgoing signals $Z_1$ to $Z_N$ of the photomultiplier tubes PMT1 and PMTN are passed to an electronic circuitry 16 which translates the signals $Z_1$ to $Z_N$ into $X_c$ and $Y_c$ (spatial corrected) position coordinate signals and a $Z_c$ (energy corrected) signal. Electronic circuitries like this one with the numeral 16 are well known in the art. One of them is for example described in detail in the U.S. Pat. No. 4,323,977 (Arseneau) or in the U.S. Pat. No. 4,316,257 (Del Medico et al.). Therefore, a more detailed description seems not to be necessary.

As can be seen from FIG. 2 the position coordinate signals $X_c$ and $Y_c$ are passed to the horizontal deflection amplifier 18 and a vertical deflection amplifier 20 of a cathode ray tube 22. The unblank control signal $U_B$ enables the cathode ray tube to illuminate a point on the screen corresponding to the location of the event, a display process in routine use with scintillation cameras.

The $X_c$ and $Y_c$ signals are also led to an analog-to-digital converter 24 and an analog-to-digital converter 26, the outputs of which are connected to a register select table 28.

Figure 3:
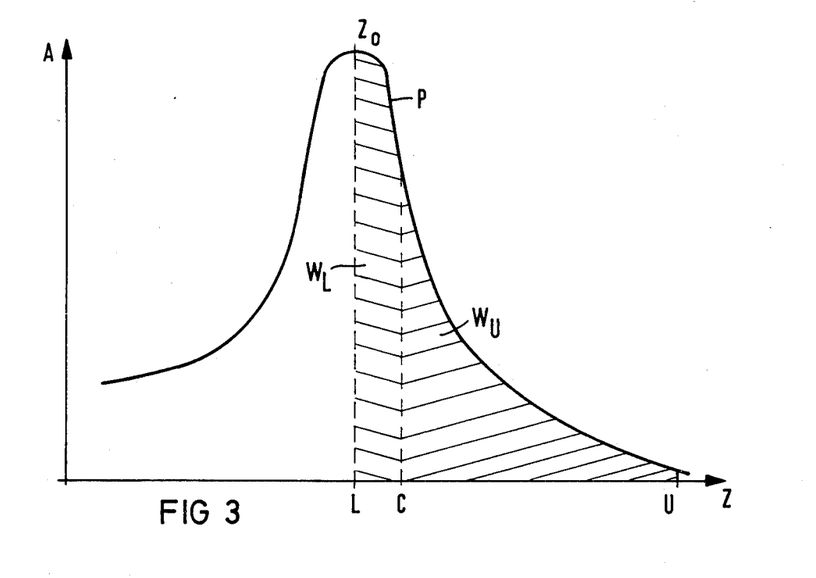
FIG. 3 is a diagram showing a local Z-signal spectrum limited by the energy windows of a divided energy window analyzer.

For tuning purposes, the energy signal $Z_c$ is fed into a first energy window analyzer 30 and it is also fed into a second energy window analyzer 31. The first energy window analyzer 30 produces one output logic pulse for each such energy signal which falls into an adjusted first (upper) energy window $W_u$ having an upper energy limit U and a lower limit C. The second energy window analyzer 31 produces one output logic pulse for each such energy signal which falls into an adjusted second (lower) energy window $W_L$ having an upper energy limit C which equals the lower limit of the first window and a lower limit L. This situation is more precisely described in the diagram of FIG. 3, which shows a local Z-signal spectrum A (Z) comprising a photopeak P, limited by the limits U, C of the first (upper) window $W_u$ of the first energy window analyzer 30 and by the limits L, C of the second (lower) window $W_L$ of the second window analyzer 31. In FIG. 3, for example, the lower window $W_L$ has its lower limit L at the center $Z_o$ of the photopeak P and its upper limit C about ¼ the way down from the top of the photopeak on the right side. The upper window $W_u$, which is about six-times wider than the lower window $W_L$, has its lower limit at C and its upper limit U at a place where the photopeak has essentially vanished.

The output signals of the first energy window analyzer 30 are passed to a first arrangement of counters 34a to 34N and the output signals of the second energy window analyzer 31 are also guided to a second arrangement of counters 36a to 36N. Each of the counters 34a to 34N and 36a to 36N have a pair of control inputs, the first ones of each pair are select control inputs 38a to 38N and 40a to 40N. The second ones of each pair are reset control inputs 42a to 42N and 44a to 44N. The select control inputs 38a to 38N and 40a to 40N receive select pulses from the register select table 28 via line 46. The reset control inputs 42a to 42N and 44a to 44N receive reset pulses from the register select table 28 at the end of a selected count via line 48.

Each pair of the counters are associated with the tuning point of each photomultiplier tube PMT1 to PMTN via the register select table 28 according to the location ($X_c$, $Y_c$) of the event. For instance the pair of counters 34a, 36a are associated with the tuning point of photomultiplier tube PMT1, the pair of counters 34b, 36b are associated with the tuning point of photomultiplier tube PMT2 etc., and last the pair of counters 34N, 36N are associated with the tuning point of photomultiplier tube PMTN.

The selection is only done by the register select table 28. Thus, when a radiation source 60 is positioned over a photomultiplier tube, such as PMT2 for example as indicated in FIG. 2, almost all event coordinates are in the vicinity of the center of PMT2 (i.e. the tuning point), so that nearly every event selects the register pair 34b, 36b, through the select table 28 via line 46 and select control inputs 38a, 40a to 38N, 40N.

Each selected pair of counters accumulates the count rates $N_{ui}$ in the window of the first (upper) window analyzer 30 and the count rates $N_{Li}$ in the window of the second (lower) window analyzer 31.

Thus, for example, the counter 34a delivers a count rate $N_{U1}$ (PMT1) and the counter 36a delivers a count rate $N_{L1}$ (PMT1) with respect to the tuning point of photomultiplier tube PMT1, which are a measure of the rate of radiation impinging near PMT1. Correspondently, counters 34b and 36b deliver count rates $N_{U2}$ (PMT2) and $N_{L2}$ (PMT2) with respect to the tuning point of PMT2 which are a measure of the amount of radiation impinging near PMT2. The sums $N_{Ui}$ and $N_{Li}$ correspond in magnitude to the radiation flux impinging on corresponding tuning points i, depending on the distribution of radiation source activity over the scintillation camera field of view. Thus, the amounts of count rate with respect to all tuning points of photomultiplier tubes PMT1 to PMTN of the scintillation camera 8 are provided in parallel at the outputs of the counters 34a to 34N and 36a to 36N.

The count rates $N_{Ui}$(PMT$_i$) and $N_{Li}$(PMT$_i$) are then processed by computing circuits 62a to 62N according to the equation $$\Delta Z_i = K \cdot \frac{N_{Ui}(PMT_i) - N_{Li}(PMT_i)}{N_{Ui}(PMT_i) + N_{Li}(PMT_i)}$$

with i = 1 to N
whereby K is a constant ($\approx 10$) and $\Delta Z_i$ is the measured Z error of each tuning point.

As described before, the $\Delta Z_i$ form a z-map error vector $\Delta \vec{Z}$ which is then multiplied with the deconvolution matrix $\vec{D}$ in a multiplying unit 64. The result is a gain error vector $\Delta \vec{G}_{est}$. The gains of the photomultiplier tubes can then be adjusted with respect to $\Delta \vec{G}_{est}$, which is indicated by a display unit 66 (number display in a digital console) such that an ideal vector $\vec{G}'$ with an ideal Z-map flatness is obtained as described above. To check the Z-map status the $\Delta Z_i$ are presented to a display 68 (number display in a digital console).

The deconvolution matrix $\vec{D}$ is read from a deconvolution matrix memory 70 for multiplication with the $\Delta \vec{Z}$ vector. As described above this matrix is measured and calculated in off-line measurement once for each camera design. Off-line measurement refers to the gain calibration mode of operation as opposed to on-line measurement or the normal operational used in patient diagnosis.

For this case circuitry 84, comprising an adding device 72, a ratio former 74, a calculator 76 and a matrix memory 70 are connectable to the outputs of the individual PMT output signals $Z_1$ to $Z_N$, via a signal line 78 and signal analog-to-digital converter 80, all being calibration tools attached for the off-line measurement phase only.

The adding device 72 forms the total energy status signal according to the equation $$Z_i = \sum_{j=1}^{N} Z_{ij}$$

for each position of the calibration source 60 placed sequentially over each PMT location i.

The ratio former 74 forms the ratios $C_{ij} = Z_{ij}/Z_i$, for all combinations of source locations i and PMT j signals.

The calculator 76 finally calculates from the contribution matrix $\vec{C}$ to deconvolution matrix $\vec{D}$ according to the equation $\vec{D} = \vec{C}^{-1}$. The deconvolution matrix $\vec{D}$ is then stored in the deconvolution matrix memory 70 for later utilization in on-line measurement.

Thus according to the above, all elements 24 to 28 and 34 to 68 together form a circuit 69 for tuning the radiation detectors of a radiation detection system, such as the photomultiplier tubes of a gamma scintillation camera in a parallel tuning algorithm. The elements 70 through 80 together, however, form a circuit 84 for providing the deconvolution matrix $\vec{D}$ to the tuning circuit 69.

The circuit 69 is only one embodiment of the present invention. A further possible embodiment, which is a modification of the embodiment of FIG. 2 is shown in FIG. 4 for example.

Figure 4:
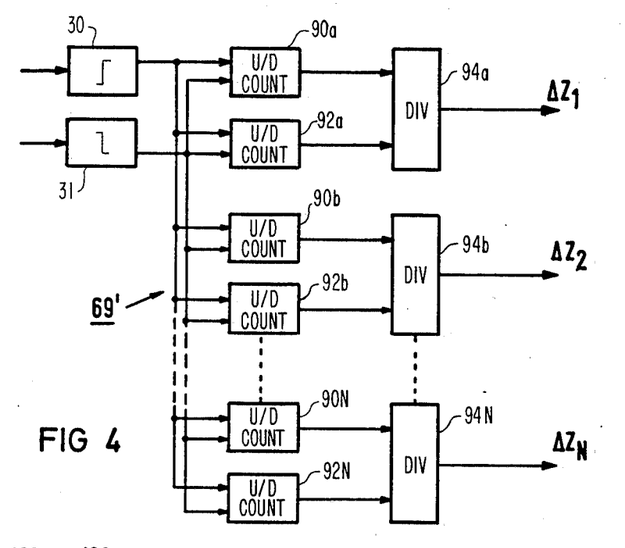
FIG. 4 shows a modification of the block circuit diagram of FIG. 2.

FIG. 4 for example shows a modification, wherein up and down counters 90a to 90N are provided to calculate directly the count differences $N_{Ui}$ (PMT$_i$)–$N_{Li}$ (PMT$_i$) with respect to the divided windows of the energy window analyzers 30 and 31. Counters 92a to 92N are provided for directly accumulating the counts of both windows according to $N_{Ui}$ (PMT$_i$)+$N_{Li}$ (PMT$_i$). The computing circuits 62a to 62N of the embodiment of FIG. 2 are then simplified to mere ratio formers 94a to 94N as indicated in the embodiment of FIG. 4.

Block diagrams have been used in FIGS. 2 and 4 to provide illustrative embodiments of the invention since the various components used therein are well known in the art. For example, counters, up/down counters and, accumulators, as well as window circuits, are of the traditional type such as disclosed in U.S. Pat. No. 4,296,320 issued to S. Miller on Oct. 20, 1981.

Figure 5:
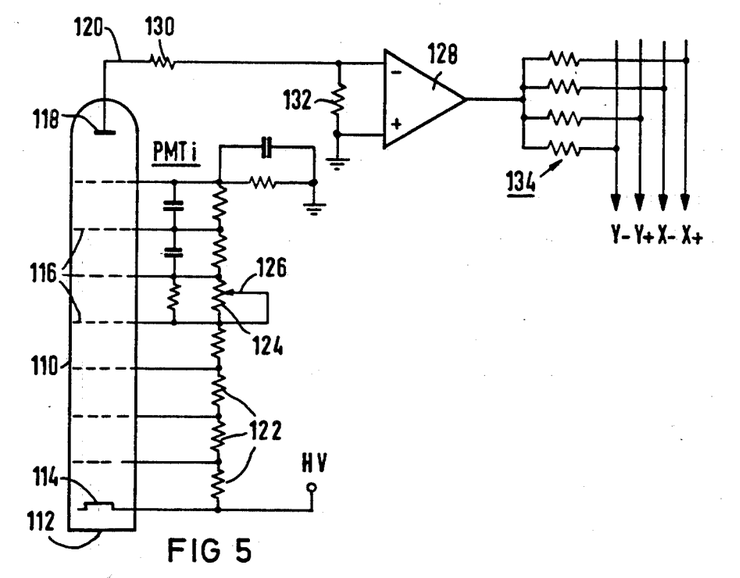
FIG. 5 shows a typical photomultiplier tube, comprising means to enable adjusting the gain of the tube.

FIG. 5 shows a typical photomultiplier tube PMT$_i$ comprised of an evacuated envelope 110 having a light input window 112 which, in connection with FIG. 2 is optically coupled to the scintillation crystal 10 of the camera 8. This typical photomultiplier tube has a photocathode 114 to which a high voltage HV, typically 1 to 2 kilovolts below ground, is applied. The photomultiplier tube has a plurality of dynodes or intermediate electrodes 116 that cause electron multiplication and yield electrons which are directed to anode 118 on which the output signal is developed corresponding with scintillation energy, on its output line 120. The dynodes have potential distributing resistors such as those marked 122 connected between them. One group of resistors including resistor 124 is made variable or as a potentiometer whose arm 126 is movable to enable adjusting the gain of the photomultiplier tube. This potentiometer is adjusted during the calibration or tuning procedure according to the present invention.

FIG. 5 also shows a typical preamplifier 128, to whose non-inverting input the signals from the photomultiplier tube are coupled through a divider comprised of resistors 130 and 132. The output of the representative preamplifier 128 is supplied to one of the resistor networks 134 which is present in the electronic circuitry 16 in FIG. 2.

There is a resistor network, not shown, for each of the photomultiplier tubes PMT1 to PMTN. As is customary, the values of the resistors in the networks are weighted so that they jointly correspond with the x and y coordinates of the photomultiplier tube which supplies them with energy signals. All of the $-x$ and $+x$ and $-y$ and $+y$ signals outputted from the respective networks are combined and processed to get the signals $X_c$, $Y_c$ and $Z_c$ at the output of the electronic circuitry 16 of FIG. 2.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims appended hereto. It will be appreciated that the selection, connection and layout of the various components of the described configurations may be varied to suit individual tastes and requirements.

What is claimed is:

1. A method for calibrating the gain of an array of radiation detectors of a radiation detection system comprising the steps of:
   (a) measuring in parallel for each radiation detector using a predetermined calibration point the energy map status, thereby obtaining an energy response vector whose elements correspond to the individual output of each radiation detector, each predetermined calibration point being a prescribed location corresponding to one of the radiation detectors;
   (b) multiplying that energy response vector with a predetermined deconvolution matrix, said deconvolution matrix being the inversion of a contribution matrix containing matrix elements $C_{ij}$, each such matrix element $C_{ij}$ of said contribution matrix representing the relative contribution level of a radiation detector j of said detection system for a point radiation source placed at a location i, thereby obtaining a gain vector product for said radiation detectors;
   (c) adjusting the gains of the radiation detectors with respect to the gain vector product such that a unity gain vector is essentially obtained;
   (d) measuring again the energy map status according to step (a); and
   (e) if the energy map status fails to essentially produce a unity gain vector repeat steps (a) to (d) until the energy map status substantially corresponds to unity.

2. A method according to claim 1, comprising the steps of
   (a) measuring in parallel for each radiation detector predetermined calibration point the energy output signals to obtain for the array of radiation detectors an energy response error vector whose elements correspond to the individual energy response signal of each radiation detector;
   (b) multiplying that energy response error vector with said predetermined deconvolution matrix, thereby obtaining a calculated gain error vector;
   (c) adjusting the gains of the radiation detectors according to said calculated gain vector such that a unity gain vector is obtained;
   (d) measuring again the energy map status according to step (a); and
   (e) if the energy map status is not yet essentially unity repeat steps (a) to (c) until the energy map status essentially corresponds to unity.

3. A method according to claim 1, wherein said contribution matrix is determined once using a known radiation point source.

4. A method according to claim 3 wherein the array includes N radiation detectors and the method further comprises the steps of
   (a) placing a radiation source at one of said predetermined calibration points (i) of a radiation detector;
   (b) measuring for each of the array of N radiation detectors the energy value ($Z_{ij}$) being the radiation detector number and i representing the placement of the source at a tuning point;
   (c) adding all N energy values ($Z_{ij}$) together for the total energy status signal ($Z_i$) according to the equation $$Z_i = \sum_{j=1}^{N} Z_{ij}$$

(d) repeating (a) through (c) for each of the N tuning points of a radiation detector; and
   (e) calculating the matrix elements ($C_{ij}$) of the contribution matrix (C) according to the equation $$C_{ij} = \frac{Z_{ij}}{Z_i}$$

5. A method according to claim 3, wherein said deconvolution matrix ($\overline{D}$) is calculated from said contribution matrix ($\overline{C}$) according to equation $\overline{D} = \overline{C}^{-1}$.

6. A method according to claim 1, wherein the radiation detection system includes photomultiplier tubes as the radiation detectors to serve as a gamma scintillation camera and the method of gain calibration provides uniform image illumination.

7. Apparatus for calibrating the gain of an array of radiation detectors of a radiation detection system, the apparatus of the type wherein a radiation source is placed in a predetermined location, the apparatus comprising:
   (a) means for measuring in parallel for each radiation detector predetermined calibration point the energy map status of each of the plurality radiation detectors whose combination of individual values provides an energy response vector;
   (b) means for multiplying said energy response vector with a predetermined deconvolution matrix, said deconvolution matrix is the inversion of a contribution matrix containing matrix element $C_{ij}$, each such matrix $C_{ij}$ of said contribution matrix representing the relative contribution level of a radiation detector j of said detection system for a point radiation source placed at a location i, thereby obtaining a calculated gain vector for said radiation detectors;
   (c) means for adjusting the gains of the radiation detectors with respect to the calculated gain vector such that a unity gain vector is obtained.

8. Apparatus according to claim 7, comprising:
   (a) means for measuring in parallel for each radiation detector calibration point the energy error signal, thereby obtaining an energy response error vector;
   (b) means for multiplying that energy response error vector with said predetermined deconvolution matrix, thereby obtaining a calculated gain error vector; and
   (c) means for adjusting the gains of the radiation detectors according to said calculated gain error vector such that an ideal gain vector is obtained.

9. Apparatus according to claim 7, wherein said contribution matrix is determined initially before gain calibration of the array of radiation detectors, the apparatus comprising:
   (a) a radiation source located at a predetermined calibration point (i) of a radiation detector;

(b) means for measuring for each radiation detector the energy value ($Z_{ij}$), being the radiation detector number and i representing the placement of the source at a tuning point;

(c) means for adding all energy values ($Z_{ij}$) together to the total energy status signal ($Z_i$) according to the equation $$Z_i = \sum_{j=1}^{N} Z_{ij}$$

(d) means for calculating the matrix elements ($C_{ij}$) of the contribution matrix according to the equation $$C_{ij} = \frac{Z_{ij}}{Z_i}$$

(e) means for calculating from the contribution matrix ($\overline{C}$) the deconvolution matrix ($\overline{D}$) according to the equation $\overline{D} = \overline{C}^{-1}$;

(f) means for storing the deconvolution matrix;

(g) means for reading the deconvolution matrix from said storing means in order to multiply said energy dependent vector with said deconvolution matrix to provide a unity gain vector.

10. Apparatus according to claim 7, wherein said radiation detectors are photomultiplier tubes of a gamma scintillation camera.

11. In a system for regulating the gain of a radiation detecting system including a plurality of detecting means responsive to radiation to produce corresponding electrical pulses each detecting means having a gain adjustment and where a known radiation source is positioned in a predetermined location being one of a plurality of predetermined locations each associated with respect to one of said detecting means, the system comprising:

(a) means for measuring the electrical pulse output of each of said detecting means to form an energy map status vector including the contribution of each of the plurality of said detecting means;

(b) means for multiplying the energy map status vector by a predetermined deconvolution matrix to produce a gain vector; and (c) means for adjusting the gain adjustment of each of the detecting means in accordance with the gain vector to provide a subsequent gain vector output from the means for multiplying that essentially corresponds to a unity gain vector.

12. In a system according to claim 11, the system including calibrating means coupled to the output of the detector means for providing the predetermined deconvolution matrix to the means for multiplying, the calibration means comprising converting means for receiving the output of the detecting means and providing a digital output, adding means for suming the digital output to provide a total, dividing means for receiving the total and the digital output to form a ratio, calculating means for performing a matrix invasion operation on a set of ratios corresponding to the plurality of detecting means, for each one of the plurality of predetermined locations, and memory means for storing the output of said calculating means to provide the predetermined deconvolution matrix for the means for multiplying.

* * * * *